(12) United States Patent
Batchelder

(10) Patent No.: US 7,017,397 B2
(45) Date of Patent: Mar. 28, 2006

(54) SURFACE ENERGY PROBE

(76) Inventor: John Samuel Batchelder, 2 Campbell Dr., Somers, NY (US) 10589

( * ) Notice: Subject to any disclaimer, the term of this patent is extended or adjusted under 35 U.S.C. 154(b) by 205 days.

(21) Appl. No.: 10/716,070

(22) Filed: Nov. 18, 2003

(65) Prior Publication Data
US 2004/0099051 A1    May 27, 2004

Related U.S. Application Data

(63) Continuation-in-part of application No. 10/067,573, filed on Feb. 5, 2002, now Pat. No. 6,697,152, which is a continuation-in-part of application No. 09/310,491, filed on May 12, 1999, now Pat. No. 6,449,035.

(51) Int. Cl.
G01N 13/00    (2006.01)
(52) U.S. Cl. ........................................ 73/104
(58) Field of Classification Search .................. 73/104, 73/866.5
See application file for complete search history.

(56) References Cited

U.S. PATENT DOCUMENTS

| 3,618,374 A | * | 11/1971 | Miller | 73/104 |
| 6,287,388 B1 | | 9/2001 | Hahn | 134/6 |
| 6,449,035 B1 | | 9/2002 | Batchelder | 356/237.1 |
| 6,507,393 B1 | | 1/2003 | Batchelder | 356/237.1 |

* cited by examiner

Primary Examiner—Thomas P. Noland

(57) ABSTRACT

A method and an apparatus for detecting relative changes in the surface energy of a test surface by adhering a tacky sampling surface to the test surface and removing the tacky sampling surface from the test surface while measuring the force and speed of removal. The measured force and speed of removal is used to compute a relative surface energy, which is compared to a standard value for that surface. This technique has utility for monitoring the cleanliness of surfaces in printing, adhesive and paint application, display and semiconductor fabrication, and generally test surfaces requiring cleanliness and which cannot readily be transported to or configured for an existing surface analysis technique.

18 Claims, 7 Drawing Sheets

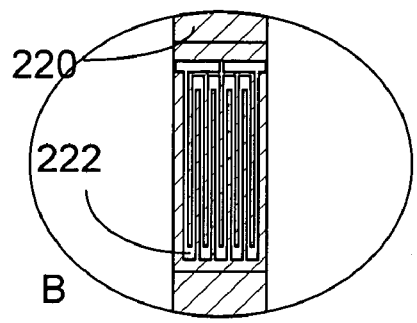
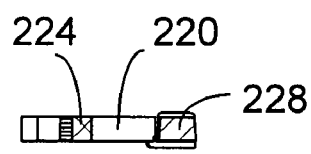
FIG. 3e          FIG. 3d
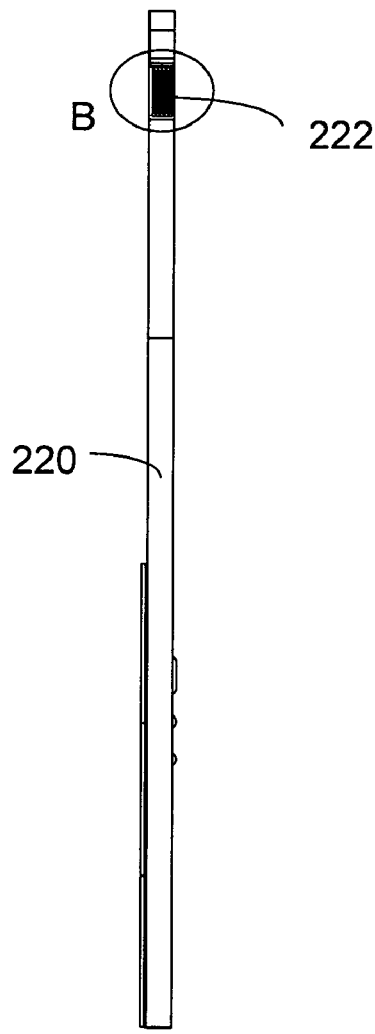
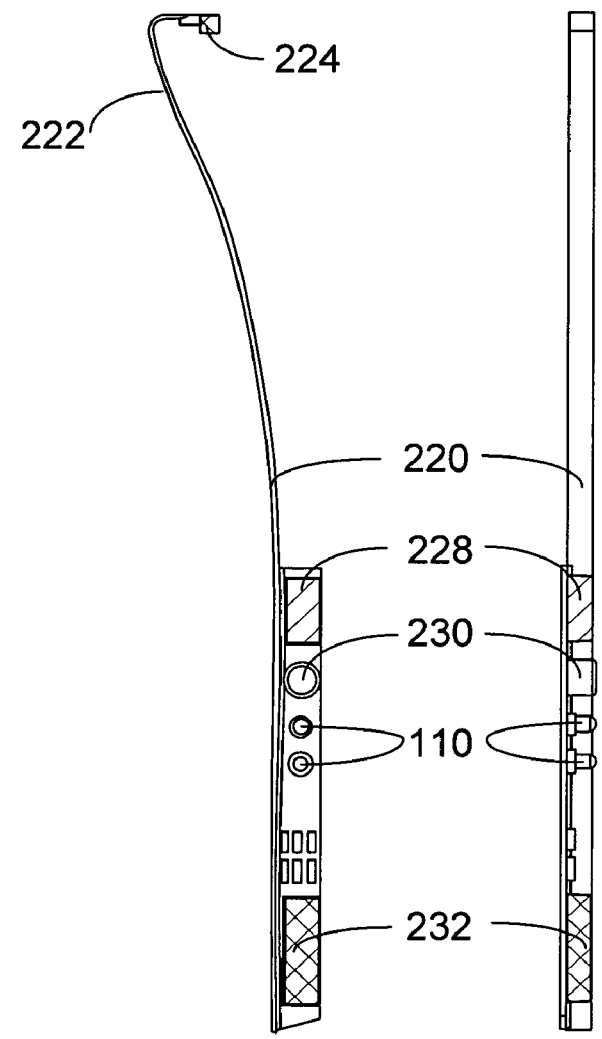
FIG. 3a          FIG. 3b          FIG. 3c

SURFACE ENERGY PROBE

RELATED APPLICATIONS

This is a continuation in part of application Ser. No. 10/067,573, filed 5 Feb. 2002, and now U.S. Pat. No. 6,697,152, which is a continuation in part of application Ser. No. 09/310,491, filed 12 May 1999, now issued as U.S. Pat. No. 6,449,035, which is incorporated herein in its entirety.

FIELD AND BACKGROUND OF THE INVENTION

A clean surface has a surface energy, which is the analog of the surface tension of a liquid. The surface energy of a solid, for example, affects how well the surface of the solid is wetted by adhesives and sealants.

The ability to monitor surface energy is useful in a variety of development and manufacturing applications, and several techniques to monitor surface energy have been established. Static and dynamic contact angle measurements between a standard solvent and the test surface are described in the measurement standard ASTM D5725-99 from the American National Standards Institute. It equates the surface energy of a test surface, or equivalently its surface free energy, to the surface tension of a liquid contacting the test surface with a zero degree contact angle. This technique is implemented in the OCA 15 video-based optical contact angle measurement system from Future Digital Scientific in Long Island, N.Y. The test surface is placed on the horizontal stage of the OCA 15, a liquid drop is placed on the surface, and images of the drop and surface are analyzed.

Peel test measurements are commonly done to measure adhesive joint quality. The ASTM D 1876 standard from the American National Standards Institute is a peel test for evaluating a bond between two flexible substrates. This and related techniques are implemented in the Motorized Peel Tester from Imada of Northbrook, Ill. Generally peel test results are weakly dependent on the surface energy of the adherends prior to bonding, since bond failure predominantly occurs in the adhesive and not at the interfaces between the adhesive and the adherends. However, for the case where the two adherends are of the same material, and when they are peeled apart they separate at their interface with no work being expended to distort the material, the work required to separate the two materials is twice the surface energy of the material.

Atomic force microscopy can measure surface energy directly by touching a probe tip to the surface under test and then measuring the force required to withdraw the tip from the test surface. This technique is implemented in the commercially available atomic force microscope from Hysitron of Minneapolis, Minn.

As the test surface becomes contaminated with atoms or molecules of dissimilar materials, the surface energy can change. For example, droplets of a vapor phase contaminant can wet and spread out on the surface if the surface tension of the liquid is less than the surface energy of the surface; the resulting contaminated surface will usually has a lower resulting surface energy.

Films or sub-monolayers of contaminating atoms or molecules on a surface are called molecular contamination. Such contamination has long been known to be a detractor in the application of paints, adhesives, and sealants. More recently, the importance of molecular contamination in display, semiconductor, and nano-materials fabrication has prompted the development of dedicated sensing techniques like the AiM-100 from Particle Measurement Systems of Boulder, Colo. This technique detects mass changes on the surface of a surface acoustic wave device; an increase in mass on the surface can be the signature of molecular contamination deposited on the surface.

DISCLOSURE OF INVENTION

This invention is a method and an apparatus for detecting relative changes in the surface energy of a test surface by adhering a tacky sampling surface to the test surface and removing the tacky sampling surface from the test surface while measuring the force and speed of removal. The measured force and speed of removal is used to compute a relative surface energy, which is compared to a standard value for that surface. This technique has utility for monitoring the cleanliness of surfaces in printing, adhesive and paint application, display and semiconductor fabrication, and generally test surfaces requiring cleanliness and which cannot readily be transported to or configured for an existing surface analysis technique.

BRIEF DESCRIPTION OF DRAWINGS

FIG. 2b is a shows cut-away view A—A of a manipulator and a sampler specified in FIG. 2a.

FIGS. 3a through 3d are views of a printed circuit and attached components used in a preferred embodiment of the apparatus.

FIG. 3d is a magnified view B of a printed circuit and attached components specified in FIG. 3a.

Definitions

Test Surface

Figure 1:
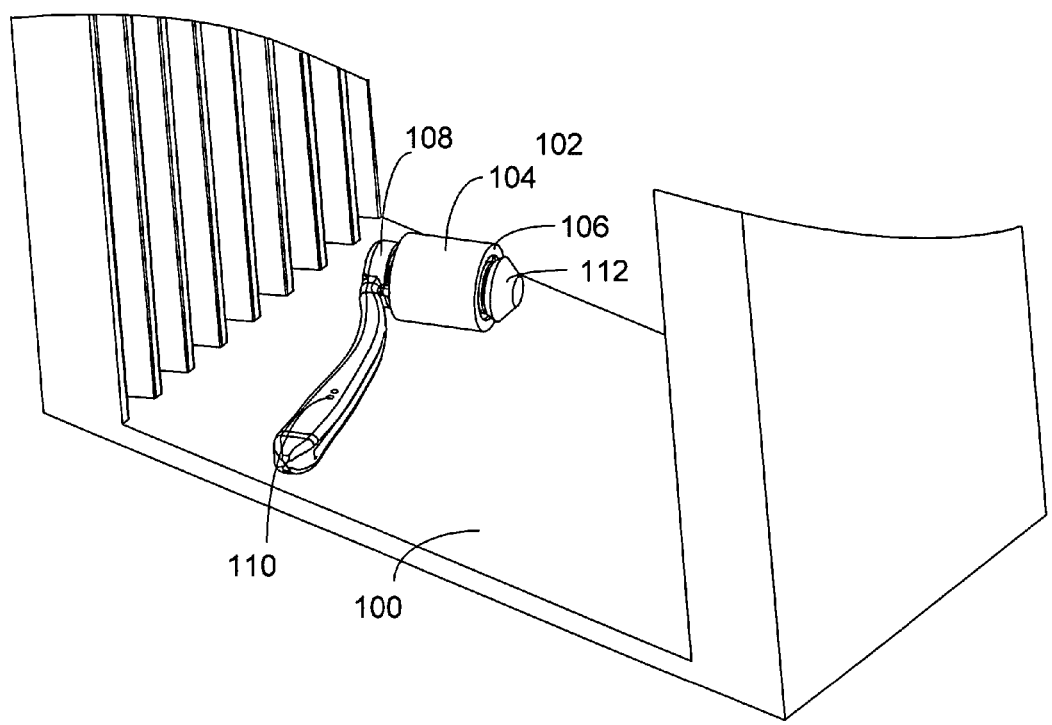
FIG. 1 is a perspective view of a preferred embodiment of the apparatus.

This invention is an improved peel test for applications where the test surface is not a small disposable sample. Examples of test surfaces to which this invention is applicable are surfaces of machine and process tools, manufactured parts, and materials prior to application of paints or adhesives.

The invention measures relative surface energy for solid test surfaces. The test surface can be rigid or flexible. The test surface need not be planar. We consider variation of the test surface from planarity on three length scales. The longest length scale is the test surface curvature, and is determined by averaging the deviations of the surface from planarity over lengths of more than roughly a centimeter; the surface curvature must be small enough so the sampler can travel parallel to the local surface while uniformly contacting the surface. The shortest length scale is the test surface roughness, and is determined by averaging the deviations of the surface from planarity over lengths of less than roughly 10 microns; the test surface roughness must be small enough that the tacky surface of the sampler will deform and intimately contact the test surface within the dwell time that the sampler is adhered to the test surface. The intermediate length scale is the asperities of the test surface, covering the range between test surface curvature and test surface roughness; asperities are accommodated to the extent possible by conformality of the sampler, discussed below. Localized features of the test surface are considered asperities, such as holes, edges, and bosses. It is desirable to sample as much of the test surface as possible, however there may be obscured surface in the vicinity of an asperity.

Sampler

The sampler in this invention is a conformal tacky surface mountable on a mandrel so that it can be applied and removed from a test surface. Since a sampler will be placed in intimate contact with surfaces of uncertain cleanliness, it will probably become contaminated and require cleaning or replacing. It is preferable, therefore, that the sampler be a relatively inexpensive and disposable.

For specificity and brevity we will subsequently describe as 'tacky' a surface that has been engineered to removably adhere to the test surface. A tacky surface with too strong an adhesive bond to the test surface can exhibit failure mechanisms. One such failure mechanism is cohesive failure of the sampler adjoining the tacky surface; this can lead to depositing portions of the tacky material on the test surface. Another failure mechanism is forming permanent adhesion of the tacky surface to the test surface. A tacky surface with too weak an adhesive bond will generate too little force to generate meaningful relative surface energy data.

Mandrel

The mandrel engages the sampler, and it is attached to the manipulator through a rotary joint. The engagement mechanism is selected to be appropriate to the sampler.

Manipulator

The manipulator positions the mandrel so that 1) the sampler engaged to the mandrel is first brought into contact with the test surface, 2) the tacky surface of the sampler is successively adhered and removed from the test surface, and 3) the sampler is removed from the test surface. For brevity and specificity, we will subsequently refer to the process of successively adhering and removing the tacky surface of the sampler and the test surface as rolling the sampler, and we include geometries such as a cylindrical roller, a conical roller, application and removal of a sheet, and application and removal of an endless loop.

DESCRIPTION OF A PREFERRED EMBODIMENT

FIG. 1 is a perspective view of a relative surface energy probe 102 being applied to a test surface 100. The test surface shown is an inner surface of a semiconductor mini-environment, however it can be an arbitrary solid surface. The relative surface energy probe 102 has a manipulator 108 in the form of a handle for manually positioning the probe 102. A mandrel 106 is attached to the manipulator 108 through a rotary joint. A sampler with a tacky surface 104 is engaged to the mandrel 106, actuated by a knob 112, as will be subsequently described. Control indicator LEDs 110 provide prompting to the operator as to the relative surface energy.

A tacky surface 104 for testing high surface energy surfaces, such as the native oxide found on silicon monitor wafers, needs to have relatively low adhesion forces, so that the adhesion between the test surface and the tacky surface does not exceed the cohesive forces within the tacky material. The tacky surface found on clean room removable tape model 1310 from the UltraTape Industries of Oregon, is removable without significant residue when applied to monitor silicon wafers. A higher tack such as that found on model 4658F tape from the 3M Company of Minnesota, US, is appropriate for lower surface energy test surfaces such as polycarbonate. U.S. Pat. No. 5,902,678 describes a pressure sensitive adhesive on a flexible backing that demonstrates good particle removal characteristics. U.S. Pat. No. 5,187,007 describes a pressure sensitive adhesive used in wafer dicing; the characteristics of this film make it useful as a tacky surface in the following embodiments. The tacky films sold by Gel-Pak Corporation predictably adhere and release from test surfaces. A preferred embodiment for the tacky material is a hydrophilic polyurethane. Preferred additives to the tacky material include additives to improve ionic and electronic conduction of the tacky material so that it can dissipate static electricity; a useful maximum resistivity for the tacky surface is $10^{12}$ ohms per square centimeter. Those skilled in the art will appreciate that there is a spectrum of possible compositions for the tacky material, and that a particular test surface may require a specialized tacky surface.

In a preferred embodiment of the tacky surface 104, the tacky material forming the tacky surface is of sufficient thickness that the tacky surface can deform to intimately contact the test surface in the presence of test surface roughness. A preferred thickness of the tacky material is between 0.1 and 2 millimeters. A preferred dwell time during which this deformation should occur is between ten of milliseconds and 10 seconds. A preferred pressure available to urge this deformation varies between 200 Pascals and 200,000 Pascals.

A sampler comprises a tacky material, forming the tacky surface 104, and a support for the tacky material. A preferred embodiment for the support is a generally cylindrical tube formed of Mylar, Kapton, Teflon, polyethylene, polyvinyl, metal foil, rubber, or other flexible material. The support can include a conformal layer such as closed cell acrylic foam to improve the ability of the tacky surface to conform to asperities of the test surface. If such a conformal layer is used, it is preferable to include a vapor barrier such as an aluminum film between the conformal layer and the tacky surface to minimize the migration of contaminants such as plasticizer to the tacky surface.

The sampler is preferably stored with several barriers protecting the cleanliness of its tacky surface. One preferred barrier is a strippable film placed in direct contact with the tacky surface. Examples of strippable film include Teflon, polypropylene, and polyethylene. In a preferred embodiment the strippable film contains little or no plasticizer. Another preferred barrier is to enclose the sampler in a container like a box or bottle. The sampler can be adhered to the lid or cap of the container by applying tacky material to the inside of the lid or cap. Another preferred barrier is to bag the samplers in clean plastic bags. These barriers can be used separately or in combination.

In a more preferred embodiment, the manipulator 108 is a handle held by an operator. This has advantages that the operator can roll the sampler on an arbitrarily oriented test surface.

In a preferred embodiment the mandrel 106 comprises a conformable layer adjacent to the engagement surface. An example of such a conformable layer is a cylinder of Poron polyurethane foam with a thickness between 0.3 and 10 millimeters and a Shore A durometer of less than 40.

In a preferred embodiment the mandrel 106 comprises a feature to aid in measuring the rotation rate of the mandrel around the rotary joint. A preferred embodiment for a sensor is a Hall sensor on the manipulator positioned to sense the motion of a permanent magnet in the mandrel 106.

Figure 2A:
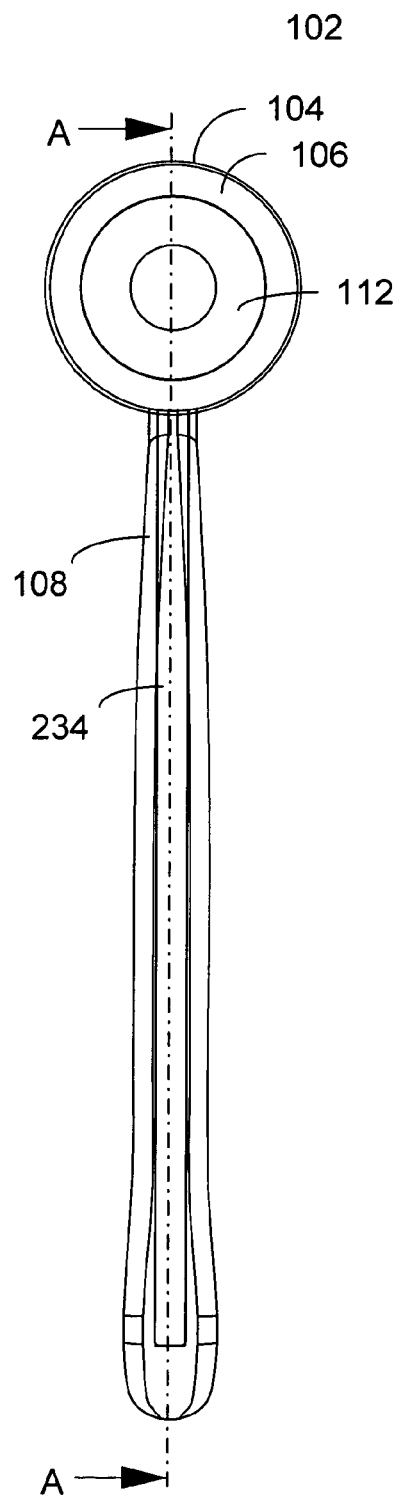
FIG. 2a is a perspective view of a manipulator and a sampler.
Figure 2B:
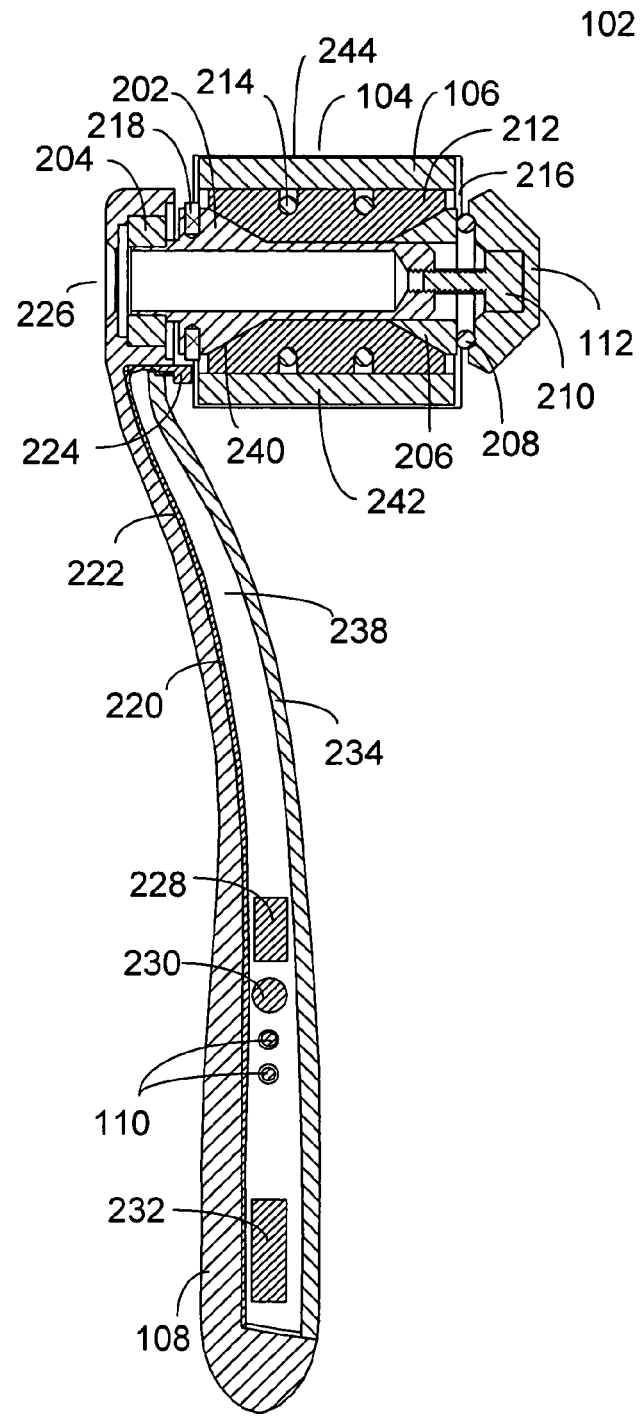

FIG. 2a shows a plan perspective of the probe 102 from FIG. 1. FIG. 2b shows the cross section A—A specified in FIG. 2a. The manipulator 108 further comprises a cavity 238 enclosed by a cover 234. A printed circuit 220 in the cavity 238 interconnects several electronic components, including a controller 232, the indicators 110, a battery 230, a signal conditioner 228, a strain gage 222, and a Hall sensor 224.

A ball bearing 204 joins the manipulator 108 to the mandrel 106. The mandrel 106 comprises a core 202 with a conical surface 240, permanent magnets 218 to drive the Hall sensor 224, a Teflon segmented cylinder 212 bound by o-rings 214, a compliant layer 242, a sliding conical wedge 206, a screw 210 that mates with a threaded hole in the metal core 202, a knob 212 press fit onto the screw 210, and an o-ring 208 at the interface between the knob 208 and the conical wedge 206. The ball bearing 204 is preferably a double sealed bearing rated for clean room use. The core 202 is preferably composed of anodized aluminum. A hole 226 through the manipulator 108, the bearing 204, and the core 202 allows the probe 102 to be engaged on an axle so that the tacky surface 104 may be inspected by a technique such as a darkfield microscopy.

The sampler support 244 is a cylinder of Kapton film 50 microns thick, onto whose convex surface a coating of tacky material has been applied, forming a tacky surface 104. The sampler is engaged on the mandrel by the action of turning the knob 112 with respect to the mandrel 106. This causes the conical wedge 206 and the conical surface 240 of the core 202 to be driven under the ends of the segmented cylinder 212, which uniformly expands the effective radii of the segmented cylinder 212 and the compliant layer 242.

FIGS. 3a through 3d show orthogonal views of the printed circuit 220 and the attached components with which it interconnects. FIG. 3e is an exploded view of portion B of FIG. 3a. Strain gage 222 is attached to the inner surface of the manipulator cavity 238 in the assembled probe 102 so that the signal from the strain gage 202 measures the force applied by the manipulator 108 to the mandrel 106 while rolling the tacky surface 104 over the test surface 100. The output of the strain gage 222 is conditioned by a signal conditioner 228, such as a ZMC31050. The signal conditioner output is a force signal, which is transmitted to the controller 232, such as a PIC18F248. The output of the Hall sensor 224 is a rotary motion signal, which is also transmitted to the controller 232. A battery 230 operates the circuitry associated with the printed circuit 220. The controller can sleep unless changes in the force or rotary motion signals are detected, so that no external power switch is required.

In a preferred embodiment there are memory locations accessible by controller 232 in which force and rotary motion signals are stored. There are additional memory locations in which a nominal surface energy is stored.

Figure 4:
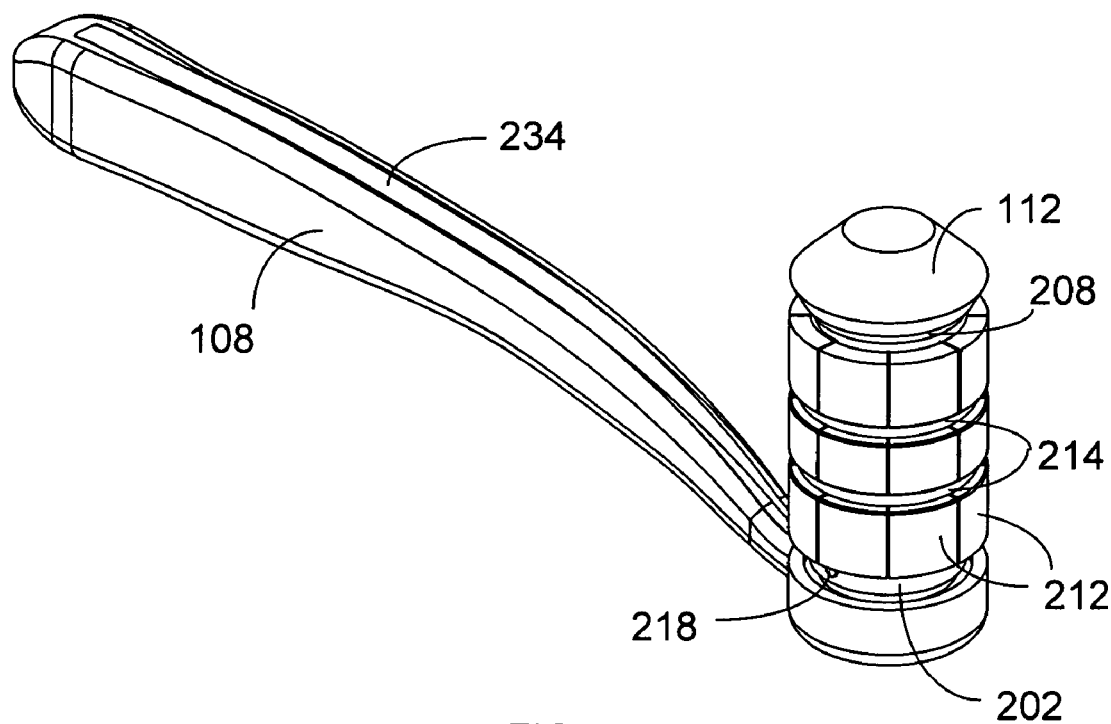
FIG. 4 is a perspective view of a sub-assembly of a preferred embodiment of the apparatus, including a handle and an expandable mandrel.

FIG. 4 shows a perspective view of the probe with the sampler and compliant layer removed for clarity.

Figure 5A:
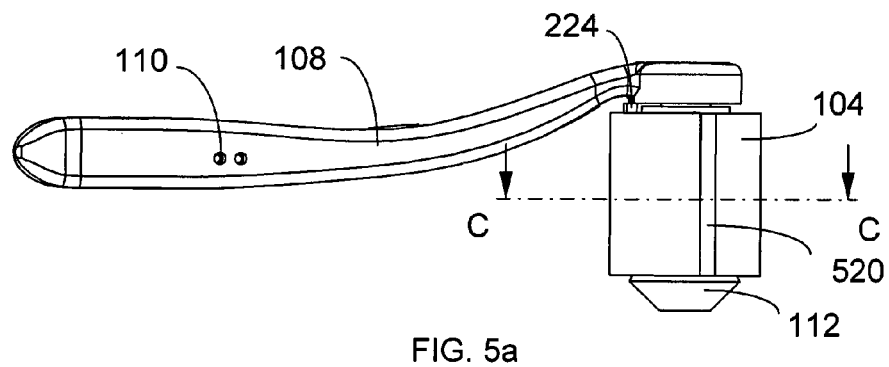
FIG. 5a is a perspective view of a preferred embodiment of a sampler.

FIG. 5a shows a perspective view of the probe. A low tack portion 520 of the tacky surface 104 allows the probe to be more easily removed from the test surface. As the sampler is moved parallel to the test surface, part of the tacky surface of the sampler is sequentially adhered to and then removed from the test surface. If the entire sampler tacky surface has a high tack, removing the sampler from the test surface can require a disadvantageous amount of force. If, instead, the sampler is positioned with the low tack portion in contact with the test surface, the sampler is easily removed from the test surface.

Figure 5B:
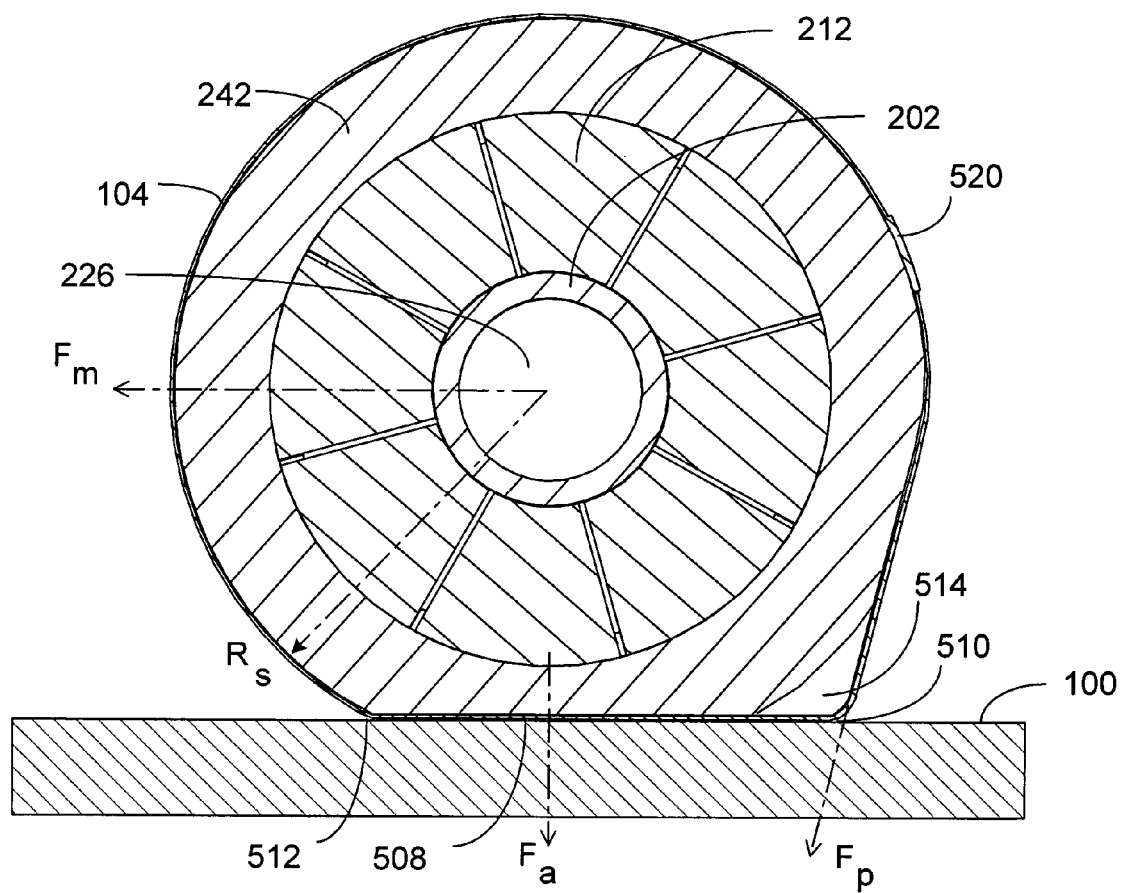
FIG. 5b is a cut-away view C—C showing some features of a sampler being applied to a test surface.

FIG. 5b shows a cross section of the probe at the line C—C of FIG. 5a. A force in the direction Fm urges the core 202 to move parallel to the test surface 100. A force Fp removes or peels the tacky surface 104 from the test surface 100 in a peeling region 510.

A resultant force Fa compresses the compliant layer 242, creating a region 512 where the tacky surface 104 is being applied to the test surface 100 and a region 508 where the tacky surface 104 is being compressed into intimate contact with the test surface 100. Rs is the radius of the tacky surface 104 in the preferred embodiment where the tacky surface is cylindrical. In a preferred embodiment an air gap 514 can form adjacent to the peeling region 510.

If the tacky surface of the sampler were composed of the same material as the test surface, and if no work is performed in deforming any portion of the sampler or the test surface except to separate the sampler from the test surface at their interface, the surface energy $\gamma$ of the test surface would be $\gamma = Fn/(2\ W\ Vs)$, where Fn is the constant force normal to the test surface required to peel a tacky surface of width W with a velocity Vs. For a robotic manipulator, the velocity Vs is usually the known spatial velocity of the manipulator, otherwise Vs is related to the observed mandrel rotation rate Rm and sampler contact radius Rs as $Vs = 2\ \pi\ Rm\ Rs$. The sampler and the mandrel will probably deform, however, increasing the required peel force above Fn. The force Fm applied to the mandrel parallel to the test surface is generally proportional to the peel force Fn. Taking these deviations from an idealized system into account, we calculate the relative surface energy to be $(k\ Fm)/(W\ Rm\ Rs)$, where k is a constant selected to equate the relative surface energy of a known clean test surface with a surface energy of that test surface obtained by an alternative technique (such as by a contact angle measurement). Additional corrections to the above formula for the relative surface energy may be necessary when the manipulator velocity is high enough that intimate contact has not occurred for the entire interface area between the test surface and the tacky surface. In a preferred embodiment the final relative surface energy is averaged to reduce random fluctuations.

In a preferred embodiment the measured relative surface energy is compared to a stored value. The stored value may be obtained from an initial measured value, or a maximal measured value, or from an alternative measurement technique. If the measured relative surface energy has changed significantly from the stored value, an indicator may prompt an operator or external database. A stored threshold value may be used to determine whether a change in the relative surface energy is significant. Molecular contamination generally reduces the surface energy of a clean surface. Assuming this is the case, the degree of molecular contamination is related to the change in the measured relative surface energy compared to the stored value.

Figure 6:
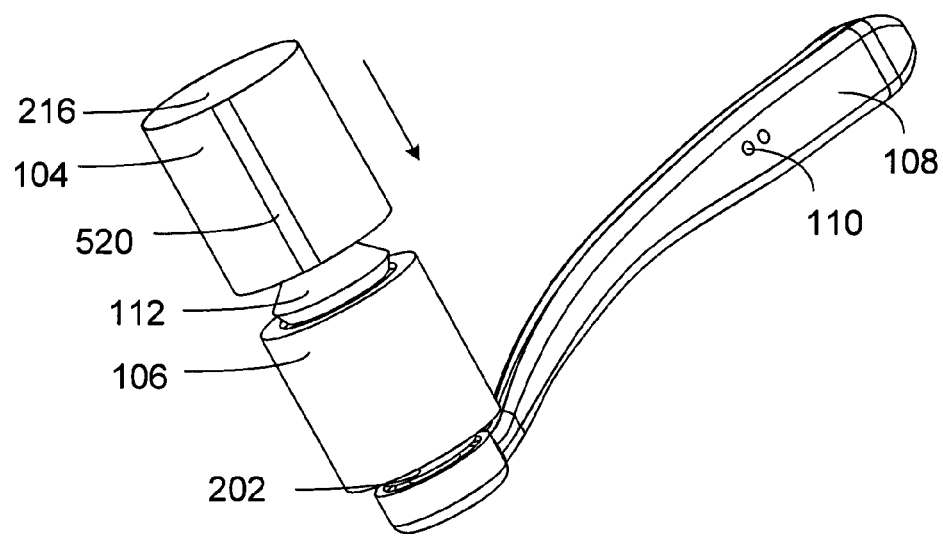
FIG. 6 is a perspective view of a sampler being engaged on a mandrel.

FIG. 6 shows a perspective view of a probe being assembled. The sampler with a tacky surface 104 is slide over the conformal surface 242 of the mandrel, then the knob 112 is turned to engage the conformal surface 242 with the surface 216 of the sampler support 244.

Figure 7:
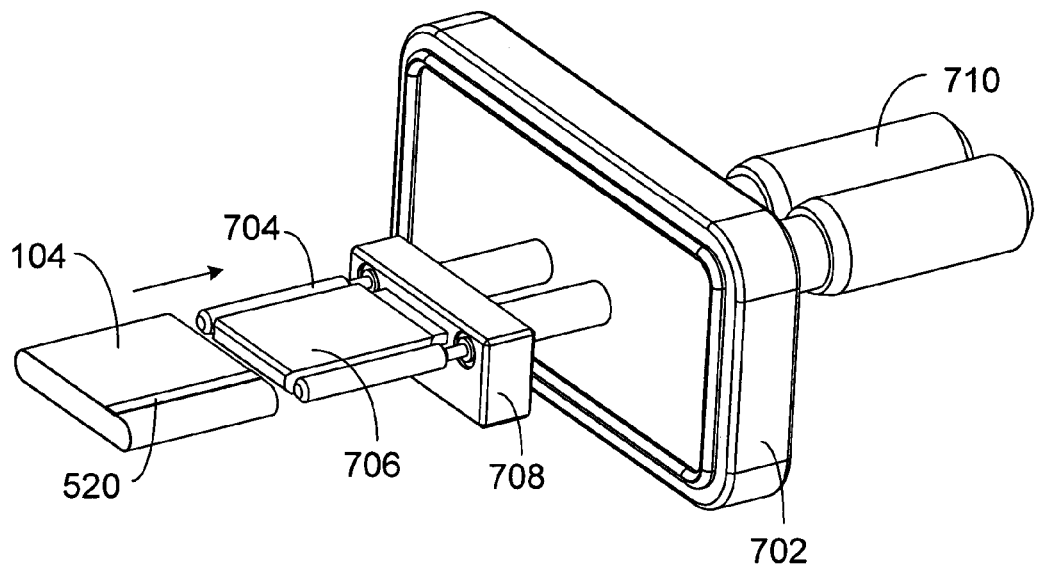
FIG. 7 is a perspective view of a sampler being engaged in a fixture for an analysis tool.

FIG. 7 shows a perspective view of a fixture for inspecting a sampler with a remote inspection apparatus such as an optical microscope, an SEM, or ion beam tool. A vacuum flange 702 holds the fixture in the inspection volume of the apparatus. The sampler with a tacky surface 104 is slid over two rollers 704 and a center support 706. The sampler with a tacky surface 104 is fixed in a viewable position in the SEM by assembling the fixture in its mating port on the SEM, and by clamping or tensioning or adhering the sampler to the fixture. Positioning controls 710 position the sampler in the inspection apparatus by rotating the rollers 704 and by moving the roller mount 708 in the axial direction of the rollers 704.

A preferred embodiment of a remote inspection apparatus is an automated darkfield microscope as described in U.S. Pat. No. 6,449,035. An axle attached to a positioner on the darkfield microscope couples to the axial hole 226 in the probe 102, allowing the tacky surface to be inspected without removing the sampler from the mandrel 106.

Figure 8:
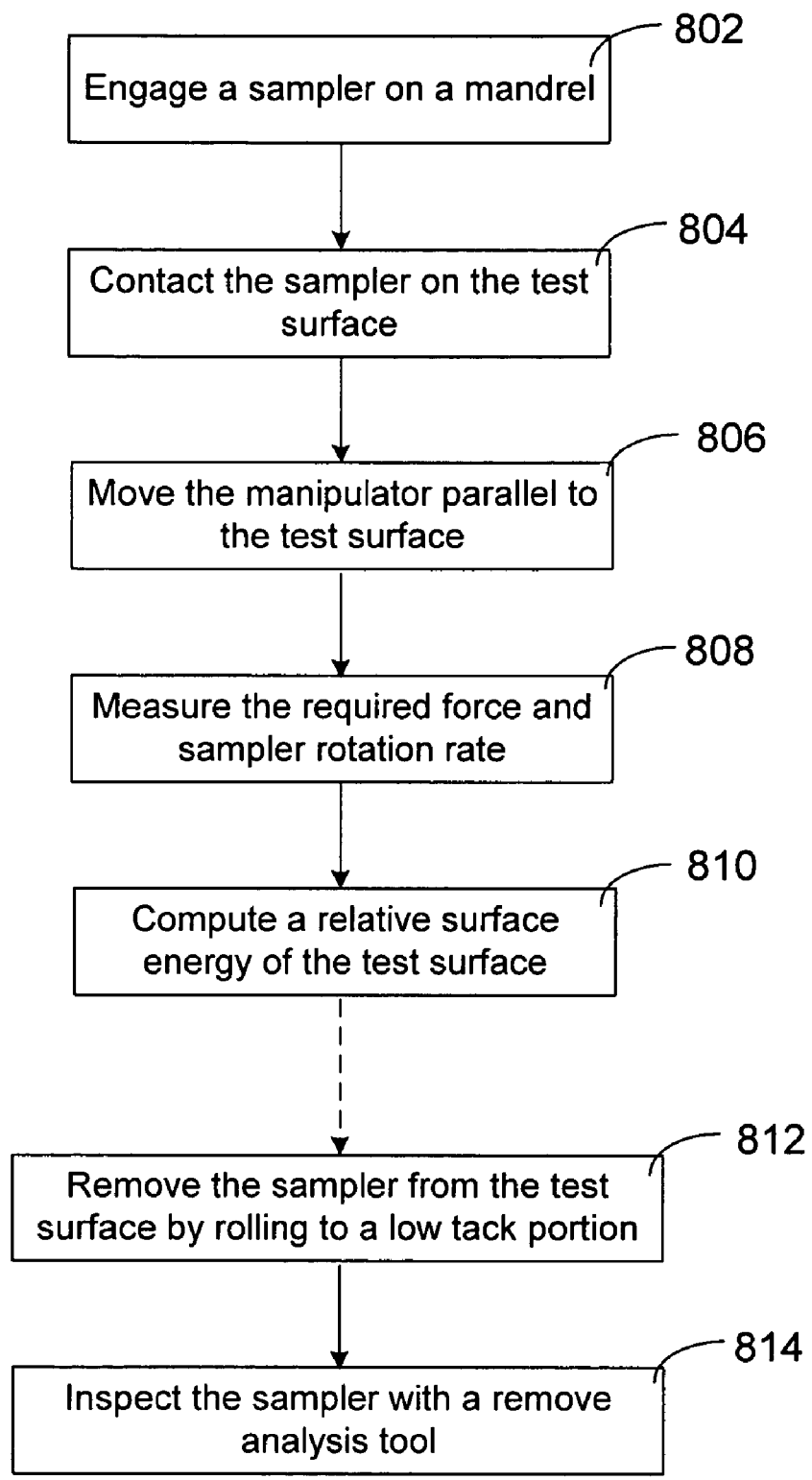
FIG. 8 shows a sequence of steps in a preferred embodiment of the method.

FIG. 8 shows the process flow of a preferred embodiment. In step 802 a sampler with a tacky surface 104 is engaged on the conformal layer 106 of a mandrel. In step 804, an operator positions the manipulator 108 so that the tacky surface of the sampler 104 contacts a test surface 100. In step 806 the operator moves the manipulator parallel to the test surface, rolling the tacky surface in sequential contact with the test surface. In step 810, sensors measure the mandrel rotation rate and the force applied by the manipulator on the mandrel in the direction of motion. In step 812, a controller 232 computes the relative surface energy of the test surface. In step 812, the operator rolls the mandrel so that the low tack portion 520 of the tacky surface 104 is in contact with the test surface, 100, and removes the tacky surface from the test surface. In step 814, the tacky surface 104 of the sampler is inspected with a remote analysis tool.

DESCRIPTION OF ALTERNATIVE PREFERRED EMBODIMENTS

In one preferred embodiment the sampler support 244 is a tube of sufficient mechanical rigidity that a radially expanding mandrel can engage the interior surface of the tube by friction. In another embodiment the support includes a rigid joint, such as an axial hole with a divot, where the rigid joint mates with a corresponding feature on the mandrel, such as a cylinder and a spring-loaded pin. The sampler may have a feature such as a tab to aid in removing the sampler from the mandrel.

In a less preferred embodiment the sampler support is a strip spooled on a supply roller. Motion of the sampler unrolls the supply roller, applies the tacky surface of the sampler to the test surface, peels the tacky surface from the test surface, and spools the strip onto the mandrel. In another embodiment the sampler support is a continuous loop supported on two or more rollers, one of which is the mandrel.

For a sampler with an engagement surface 216 which is the insider of a flexible cylinder, a preferred embodiment for the mandrel is a cylinder of variable radius; such a mandrel can be formed by axially sliding conical wedges under the ends of a segmented cylinder, or by axially compressing a cylinder of elastic material like a section of rubber tubing, or by partially unwinding a cylindrical spring. For a sampler with an axial hole with a divot, the mandrel should comprise the corresponding cylinder and spring-loaded pin.

In a less preferred embodiment, the manipulator is robotically positioned. This has advantages that the area of the test surface is well defined to which the sampler is applied, and not subject to operator variations. The rotation rate of a robotically motivated sampler is known from the velocity of the robotic motion and does not need to be measured directly.

Additional preferred embodiments for sensors measuring the rotation rate of the mandrel around the rotary joint include an optical reflector, a drive surface for a tachometer, and a clicker or other acoustic generator.

The indicators 110 shown are LEDs; in other preferred embodiments these control indicators can be audible enunciators or visual displays.

In an alternative preferred embodiment, force and rotation rate signals are transmitted to a computer or controller external to the sampler. The signals are generally buffered in memory prior to transmission. The transmission mechanism can be selected from the following: mechanical contact with electrodes on the manipulator, capacitive coupling with electrodes in the manipulator, inductive coupling with coils in the manipulator, a radio frequency emitter in the manipulator, and an optical emitter in the manipulator. In a preferred embodiment timestamp information accompanies the force and rotation rate signals, which informs the computer of the area sampled.

Although the present invention has been described with reference to preferred embodiments, workers skilled in the art will recognize that changes may be made in form and detail without departing from the spirit and scope of the invention. For example, the various features of most preferred embodiment may be used and interchanged with the alternative preferred embodiments, and vice-versa. These and other changes will be apparent to one skilled in the art.

The invention claimed is:

1. A probe for computing a relative surface energy of a test surface, comprising:
   a manipulator movable parallel to the test surface;
   a mandrel attached to the manipulator through a rotary joint;
   a sampler with a first surface engaged with the mandrel, the sampler having a convex tacky surface, a portion of the convex tacky surface contacting the test surface, wherein motion of the manipulator parallel to the test surface rotates the sampler engaged with the mandrel;
   a force sensor affixed to the manipulator for generating a force signal proportional to force applied by the manipulator to the mandrel in the direction of motion of the manipulator;
   a rotation sensor for generating a rotary motion signal in response to rotation of the mandrel; and
   a controller for receiving the force signal and the rotary motion signal; whereby the controller computes the relative surface energy of the test surface utilizing the force signal and the rotary motion signal.

2. The apparatus of claim 1, wherein the manipulator is a handle, whereby an operator manually moves the handle parallel to the test surface.

3. The apparatus of claim 1, wherein the sampler is flexible, the mandrel further comprising:
   a sampler engagement surface for engaging the first surface of the sampler; and a compliant layer adjoining the sampler engagement surface, whereby the compliant layer and the sampler engagement surface urge the sampler into intimate contact with the test surface.

4. The apparatus of claim 3, wherein the compliant layer has a durometer of less than 40 on the Shore A scale.

5. The apparatus of claim 1, wherein the sampler further comprises a compliant layer with a durometer of less than 40 on the Shore A scale.

6. The apparatus of claim 1, wherein the sampler removably engages the mandrel, the mandrel further comprising an adjustment means that selects the degree of engagement between the mandrel and the sampler.

7. The apparatus of claim 6, wherein the adjustment means is a knob that varies the radial extent of the mandrel.

8. The apparatus of claim 6, further comprising a receiver carrier for fixing a sampler in a field of view of a surface analysis tool remote from the test surface, whereby the sampler may be removed from the mandrel and the test surface, and the sampler may be fixed by the receiver carrier and examined by the surface analysis tool.

9. The apparatus of claim 1, the mandrel further comprising a coupler with a mating relationship to a coupler receiver on surface analysis tool remote from the test surface, whereby the mandrel with the engaged sampler may be coupled to the surface analysis tool.

10. The apparatus of claim 1, the convex tacky surface further comprising a surface patch with low-tack.

11. The apparatus of claim 1, wherein the rotation sensor is selected from one of the following sensors: a Hall detector embedded in the manipulator, an optical detector in the manipulator, a tachometer actuated by rotation of the mandrel with respect to the manipulator, and segmented sliding rotary electrical contacts associated with the rotary joint.

12. The apparatus of claim 1, wherein the force sensor is a strain gage affixed to the manipulator and responsive to mechanical strain in the manipulator.

13. The apparatus of claim 1, wherein the controller is a microprocessor located in the manipulator.

14. The apparatus of claim 13, further comprising a display means responsive to the microprocessor.

15. The apparatus of claim 1, further comprising:
a first memory for storing the force signal; and
a second memory for storing the rotation signal.

16. The apparatus of claim 15, wherein the controller is a computer external to the manipulator, further comprising a communication means for transmitting the contents of the first and second memory means to the computer, whereby the computer computes the relative surface energy of the test surface using the transmitted contents of the first and second memory means.

17. The apparatus of claim 1, the controller further comprising a stored nominal relative surface energy, whereby the controller computes a control indication based on the variation between the stored nominal relative surface energy and the computed relative surface energy.

18. The apparatus of claim 17, further comprising:
a stored threshold value; and
a molecular contamination indication generated by the controller when the control indication exceeds the threshold value.

* * * * *